US007654974B2

(12) United States Patent
Bass

(10) Patent No.: US 7,654,974 B2
(45) Date of Patent: Feb. 2, 2010

(54) RECLINER SPINAL TRACTION DEVICE

(75) Inventor: David B. Bass, 9737 NW. 65 Pl., Parkland, FL (US) 33076

(73) Assignee: David B. Bass, Parkland, FL (US)

( * ) Notice: Subject to any disclaimer, the term of this patent is extended or adjusted under 35 U.S.C. 154(b) by 364 days.

(21) Appl. No.: 11/096,304

(22) Filed: Apr. 1, 2005

(65) Prior Publication Data

US 2006/0224097 A1 Oct. 5, 2006

(51) Int. Cl.

| | |
|---|---|
| ***A61F 5/00*** | (2006.01) |
| ***A47B 7/00*** | (2006.01) |
| ***A47B 7/02*** | (2006.01) |
| ***A47C 3/00*** | (2006.01) |
| ***A47C 7/46*** | (2006.01) |
| ***B60N 2/02*** | (2006.01) |
| ***B60N 2/00*** | (2006.01) |

(52) U.S. Cl. ............................ 602/32; 602/33; 602/34; 602/35; 602/36; 606/237; 606/240; 606/241; 5/610; 5/616; 5/621; 5/622; 5/624; 297/284.1; 297/284.7; 297/284.8; 297/353; 297/354.1

(58) Field of Classification Search ............ 602/32–40; 606/237, 240–242, 345; 5/610, 616, 621–622, 5/624; 297/217.1, 217.3, 284.1, 284.4, 284.8, 297/354.1, 353

See application file for complete search history.

(56) References Cited

U.S. PATENT DOCUMENTS

| | | | | |
|---|---|---|---|---|
| 3,188,079 | A * | 6/1965 | Boetcker et. al. | 5/622 |
| 3,570,479 | A | 3/1971 | Horn | |
| 4,103,681 | A | 8/1978 | Shanley | |
| 4,649,905 | A | 3/1987 | Barnes | |
| 5,150,948 | A | 9/1992 | Volkle | |
| 5,423,861 | A | 6/1995 | Kelley | |
| 5,437,609 | A | 8/1995 | Leonard et al. | |
| 5,661,859 | A * | 9/1997 | Schaefer | 5/621 |
| 5,860,899 | A * | 1/1999 | Rassman | 482/142 |
| 6,027,168 | A * | 2/2000 | Crossman et al. | 297/337 |
| 6,059,365 | A | 5/2000 | Diamond | |
| 6,073,284 | A * | 6/2000 | Borders | 5/600 |
| 6,152,950 | A | 11/2000 | Shealy et al. | |
| 6,154,899 | A * | 12/2000 | Brooke et al. | 5/81.1 R |
| 6,243,897 | B1 * | 6/2001 | Sumiya | 5/610 |
| 6,276,012 | B2 * | 8/2001 | Borders | 5/622 |
| 6,336,235 | B1 * | 1/2002 | Ruehl | 5/610 |

(Continued)

*Primary Examiner*—Patricia Bianco
*Assistant Examiner*—Brandon Jackson
(74) *Attorney, Agent, or Firm*—Pablo Meles; Akerman Senterfitt

(57) ABSTRACT

A traction table (200) include a frame having a base-frame portion (202) rotatably coupled to a top-frame portion (250) at a pivot point 214, a seat back portion (208) coupled to the top frame portion, and a seat-bottom (204) slidably coupled to the frame top portion. The seat-bottom can rotate about a pivot point (262) and tilt about at least one axis (260 and/or 264). The seat-bottom can further slide forwards or backwards relative to the top frame portion. The traction table can include an optional neck piece (210) coupled to the top frame portion that can move parallel relative to the seat back portion and constructed to rotate, tilt side to side or forward and backward. The traction table can include at least one actuator motor (245 or 244) for moving the seat-bottom or neck piece relative to the top-frame portion and a controller (212) for controlling such actuator(s).

16 Claims, 9 Drawing Sheets

U.S. PATENT DOCUMENTS

| | | | | |
|---|---|---|---|---|
| 6,351,678 | B1 * | 2/2002 | Borders | 700/83 |
| 6,435,611 | B1 | 8/2002 | Walter | |
| 6,446,287 | B2 * | 9/2002 | Borders | 5/618 |
| 6,454,734 | B1 | 9/2002 | Deacon | |
| 6,592,185 | B2 | 7/2003 | Lew | |
| 6,599,257 | B2 | 7/2003 | Al-Obaidi et al. | |
| 6,626,494 | B2 | 9/2003 | Yoo | |
| 6,638,299 | B2 * | 10/2003 | Cox | 606/243 |
| 7,112,215 | B2 * | 9/2006 | Xiao et al. | 606/242 |
| 7,189,214 | B1 * | 3/2007 | Saunders | 602/32 |
| 2003/0011229 | A1 * | 1/2003 | Bell | 297/344.17 |

* cited by examiner

10

10

10

17

17

17

60

60

60

200

200

200

200

204

204

204

204

210

210

RECLINER SPINAL TRACTION DEVICE

FIELD OF THE INVENTION

This invention relates generally to traction tables, and more particularly to a traction table that is adjustable in multiple planes.

BACKGROUND OF THE INVENTION

Existing traction tables typically enable treatment in a lying supine or prone position on a flat table surface and fail to provide the comfort that might be found in a conventional recliner or executive chair. Such existing traction tables including the DRS System (K981822), the Tru-Trac Traction Table (K8893448), the Vax-D Therapeutic Table (K951622), the Saunders 3-D activetrac (K001712), and the Jilco Traction Flexion Chair (K001361) fail to include a table that reclines having a seat back portion fixed to frame and a seat-bottom and further provides relative motion and pivoting in multiple planes. In other words, existing tables generally fail to provide many degrees of freedom in terms of relative motion for initial positioning and for flexibility in providing customized treatment. In many instances, existing flat traction tables require the use of an "under the calf" leg stool to support certain positions or treatments. Furthermore, existing traction tables can sometimes use straps in awkward and/or uncomfortable positions for patients.

Additionally, many existing traction tables also fail to provide an option for cervical-neck traction. Even where such options are available in a traction table, they usually fail once again to provide many degrees of freedom to provide comfort in initial positioning and flexibility in providing customized treatment.

SUMMARY OF THE INVENTION

Embodiments in accordance with the present invention can provide a mechanical spinal traction device that can be designed in the shape of a recliner/executive chair that can provide a protocol of relief for patients that are suffering with low back pain or neck pain. Each treatment can consists of a physician prescribed amount of treatment time on the device to provide static, intermittent or pulsed traction to the neck or low back. Portions of the spinal traction device can have many degrees of freedom to provide flexibility and comfort in initial positioning and in treatment.

In a first embodiment of the present invention, a traction table can include a frame having a base-frame portion rotatably coupled to a top-frame portion, a seat back portion coupled to the top frame portion, and a seat-bottom slidably coupled to the frame top portion. Note, the seat back portion can recline where it pivots with the frame and the seat-bottom can move parallel relative to the top-frame portion. As mentioned above, the traction table can include portions with many degrees of freedom. In this regard, the seat-bottom can rotate about a pivot point and tilt about at least one axis. The seat-bottom can further slide forwards or backwards relative to the top frame portion. The traction table can further include an optional head piece coupled to the top frame portion that can move parallel relative to the seat back portion. The head piece can be constructed to rotate, tilt side to side, and tilt forward and backward. Additionally, the traction table can include one or more straps such as a strap for securing a portion of a torso to the seat back portion, a strap for securing a pelvic area to the seat-bottom, a strap for securing a thigh to the seat-bottom and a strap for securing a shin to a lower leg portion of the seat-bottom. If a head piece is included, the traction table can further include at least one strap for securing a portion of a head to the head piece. The traction table can also include at least one actuator motor for raising or lowering the seat-bottom relative to the top-frame portion and a controller for adjusting the actuator motor for at least one among a position of the seat-bottom and a traction pattern using the seat-bottom. Likewise, the traction table can also include at least one actuator motor for moving the head piece relative to the frame top portion in parallel fashion. The traction table can further include at least one sensor for automatically shunting one or more of the actuator motors used in the traction table.

In a second embodiment of the present invention, a traction table can include a frame having a frame base portion rotatably coupled to a top-frame portion, a seat back portion coupled to the top-frame portion, and a seat-bottom slidably coupled to the top-frame portion. Note again, the seat back portion can recline where it pivots with the frame base portion and the seat-bottom can tilt, rotate, and move vertically relative to the top-frame portion. The traction table can further include a head piece coupled to the top frame portion that moves vertically relative to the seat back portion. The head piece can also rotate, tilt side to side, and tilt forward and backward. The traction table can also include at least one among a strap for securing a portion of a torso to the seat back portion, a strap for securing a pelvic area to the seat-bottom, a strap for securing a thigh to the seat-bottom, a strap for securing a shin to a leg section of the seat-bottom, and a strap for securing a portion of a head to the head piece. Optionally, the traction table can further include at least one among an actuator motor for moving the seat-bottom relative to the top-frame portion in a parallel fashion along a "Z" axis, an actuator motor for moving the head piece relative to the frame top portion in parallel fashion along a "Z" axis, an actuator motor for reclining the seat-back portion on an "X" axis, and an actuator motor for moving the seat-bottom relative to the top-frame portion in a perpendicular fashion along a "Y" axis. The traction table can further include sensors used for automatically shunting at least one among the actuator motors. The traction table can also include a controller programmed to perform at least one among adjusting of the at least one actuator motor for positioning the seat-bottom, for positioning of the head piece, for altering a traction pattern using the seat-bottom, and for altering a traction pattern using the head piece.

In a third embodiment of the present invention, a traction table can include a seat back portion coupled to a frame, a seat-bottom portion slidably coupled to the frame, wherein the seat-bottom portion at least moves vertically relative to the frame, a motorized mechanism coupled to the seat-bottom portion for biasing the seat-bottom portion vertically relative to the frame, and a controller coupled to the motorized mechanism for selectively controlling the motorized mechanism.

Other embodiments, when configured in accordance with the inventive arrangements disclosed herein, can include a system for performing and a machine readable storage for causing a machine to perform the various processes and methods disclosed herein.

DETAILED DESCRIPTION OF THE DRAWINGS

Figure 1:
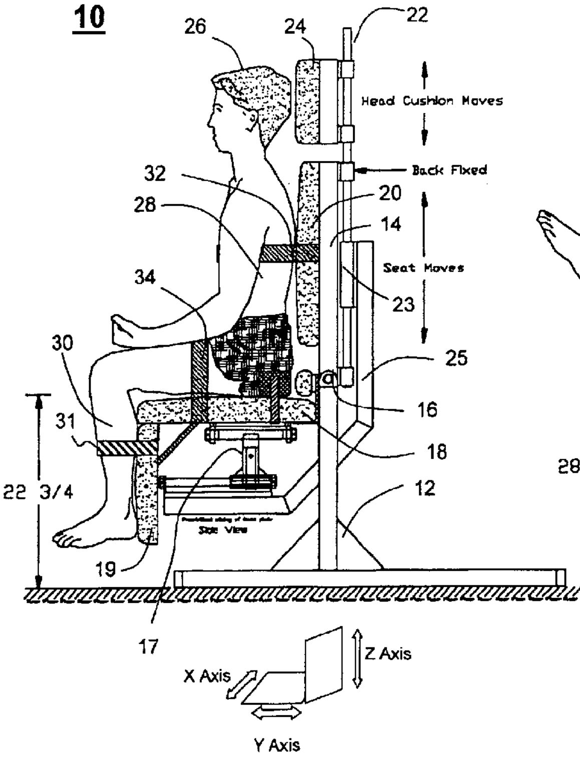
FIG. 1 is an side-view illustration of a traction table having a seat-bottom and a seat-back portion in an upright position in accordance with an embodiment of the present invention.

While the specification concludes with claims defining the features of embodiments of the invention that are regarded as novel, it is believed that the invention will be better understood from a consideration of the following description in conjunction with the figures, in which like reference numerals are carried forward.

Referring to FIG. 1 a side view of a traction table 10 designed to resemble a recliner chair and that can provide traction/distraction for patients that are suffering with low back pain (lumbar) or neck pain (cervical spine) is shown. The traction table 10 has the ability to recline from its neutral upright seat back to a full 90 degrees which has the seat back (20) parallel to the floor. A seat-bottom (18), seat-back (20) relationship is maintained as the chair reclines. So when the patient sits, similar to an executive chair, the chair/table reclines the seat-back and seat-bottom sections (18 and 20) while maintaining their perpendicular angular relationship. Such device provides a patient with an easy way of getting on and off the device and further keeps the patient in a comfortable seated "recliner" like posture during tractions/distractions. The design can avert the uncomfortable flat table mounting experienced by patients on most existing traction tables. Traction using such a device can reduce muscle spasms, enhance vertebral-bone spacing, enhance vertebral joint gliding, enhance spinal joint mechanics and reduce pains associated with these types of conditions. As with other traction devices, the repetitive use of the traction table 10 in a prescribed manner can reduce the pains associated with disc protrusions, prolapsed discs, herniated discs, facet syndromes, radiculapathies, and nerve root pressures.

Figure 2:
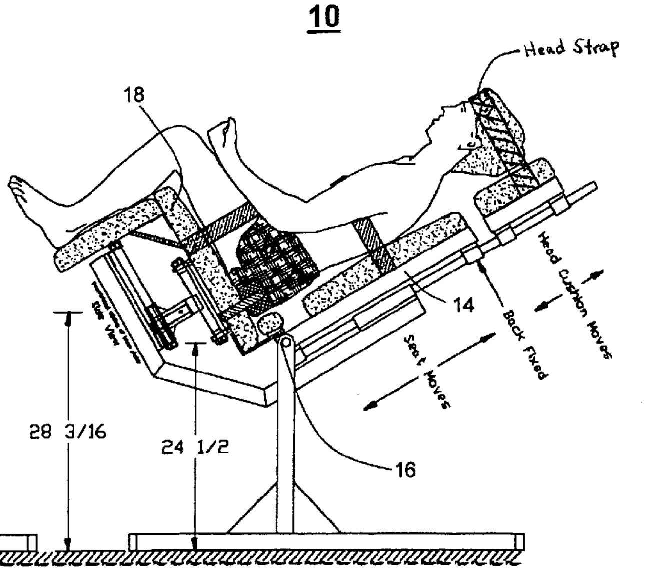
FIG. 2 is another side-view illustration of the traction table of FIG. 1 in a reclined position in accordance with an embodiment of the present invention.
Figure 5:
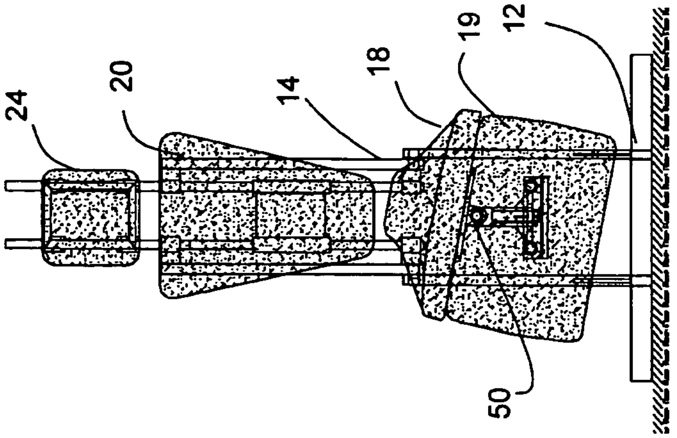
FIG. 5 is another front transparent view of the traction table of FIG. 3 with the seat-bottom tilting to a left side laterally from the perspective of a user in accordance with an embodiment of the present invention.

With further reference to FIGS. 1-5, the traction table 10 can include a frame having a base-frame portion 12 rotatably coupled to a top-frame portion 14, a seat back portion 20 coupled to the top frame portion 14, and a seat-bottom 18 slidably coupled to the top frame portion 14. The top frame portion 14 can further include or be affixed to one or more rod members 22. The seat-bottom 18 can further include or be affixed to a seat bottom base plate assembly 17, rod member or members 25, and to a member 23 having tube portions. The tube portions of member 23 enable the slidably coupled arrangement between the seat back portion 20 and the top frame portion 14 to enable parallel translation or movement between such members. Note, the seat back portion 20 can recline where it pivots (16) with the frame as shown in FIG. 2 and the seat-bottom 18 can move parallel relative to the top-frame portion 14. As will be illustrated later, the seat-bottom 18 can rotate about a pivot point and tilt about at least one axis and the seat-bottom 18 can further slide forwards or backwards relative to the top frame portion 14. The traction table 10 can further include an optional head piece 24 coupled to the top frame portion 14 that can move parallel relative to the seat back portion 20. The head piece 24 can be constructed to rotate, tilt side to side, and tilt forward and backward. Additionally, the traction table can include one or more straps (31, 32, 34, etc) such as a strap 32 for securing a portion of a torso 28 to the seat back portion 20, a strap (not shown) for securing a pelvic area to the seat-bottom 18, a strap 34 for securing a thigh to the seat-bottom 18 and a strap 31 for securing a shin 30 to a lower leg portion 19 of the seat-bottom 18. If a head piece 24 is included, the traction table 10 can further include at least one strap (not shown) for securing a portion of a head 26 to the head piece 24. The traction table can also include at least one actuator motor for raising or lowering the seat-bottom relative to the top-frame portion and a controller for adjusting the actuator motor for at least one among a position of the seat-bottom and a traction pattern using the seat-bottom. Likewise, the traction table can also include at least one actuator motor for moving the head piece relative to the top frame portion in parallel fashion. The traction table can further include at least one sensor for automatically shunting one or more of the actuator motors used in the traction table.

Figure 3:
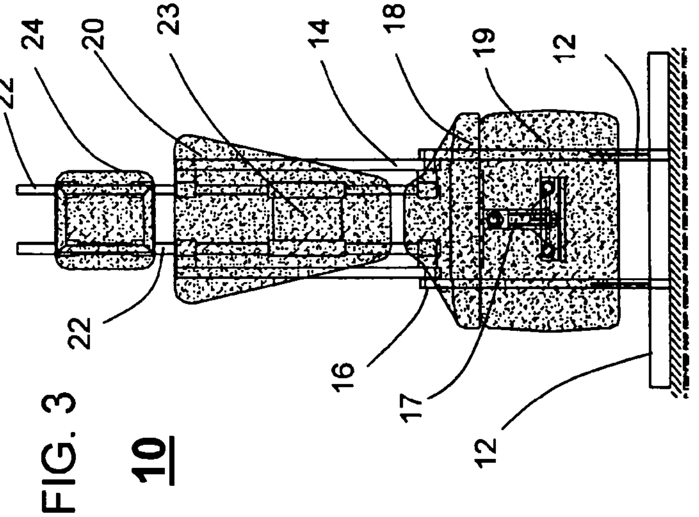
FIG. 3 is a front transparent view of the traction table of FIG. 1.
Figure 4:
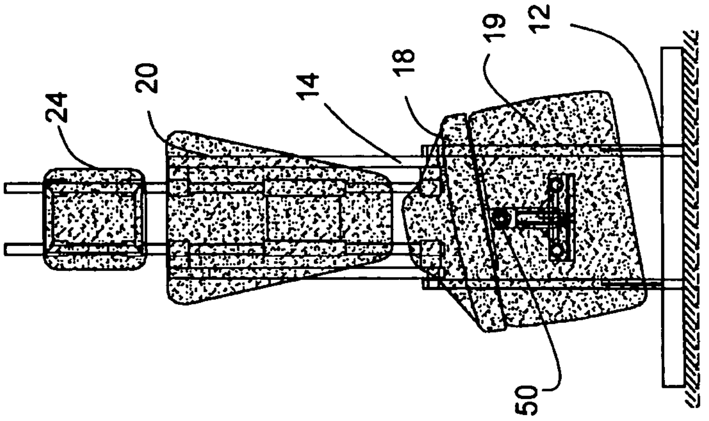
FIG. 4 is another front transparent view of the traction table of FIG. 3 with the seat-bottom tilting to a right side laterally from the perspective of a user in accordance with an embodiment of the present invention.
Figure 6:
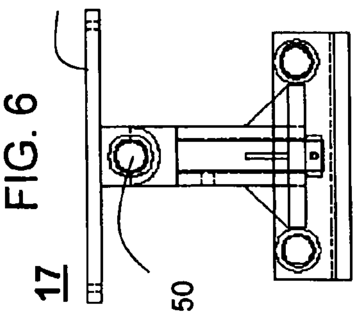
FIG. 6 is front view illustration of a base-frame portion of the traction table of FIG. 1 in a neutral position in accordance with an embodiment of the present invention.
Figure 7:
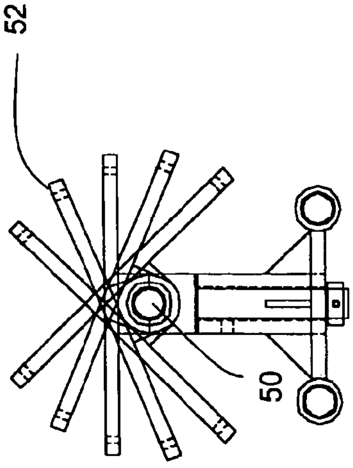
FIG. 7 is front side view of the base-frame portion of FIG. 6 illustrating the left and right lateral tilt motion of a base plate in accordance with an embodiment of the present invention.
Figure 8:
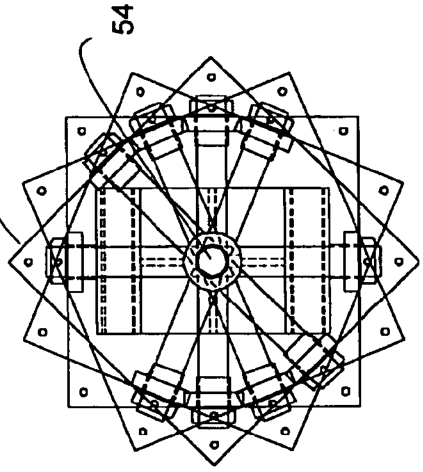
FIG. 8 is top side view of the base-frame portion of FIG. 6 illustrating the rotation of the base plate in accordance with an embodiment of the present invention.
Figure 9:
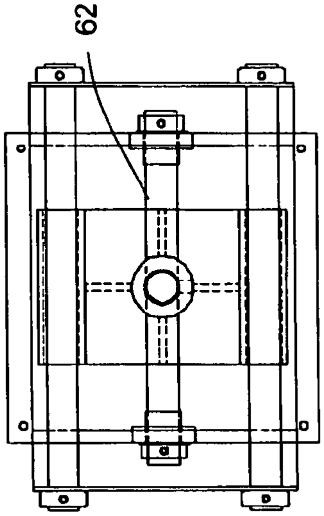
FIG. 9 is top side view of the base-frame portion of FIG. 6 along with another frame portion that rests on the ground in accordance with an embodiment of the present invention.
Figure 10:
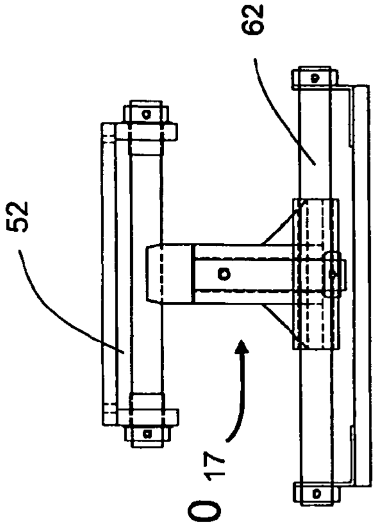
FIG. 10 is a side view of the base-frame portion of the traction table of FIG. 1 in accordance with an embodiment of the present invention.
Figure 11:
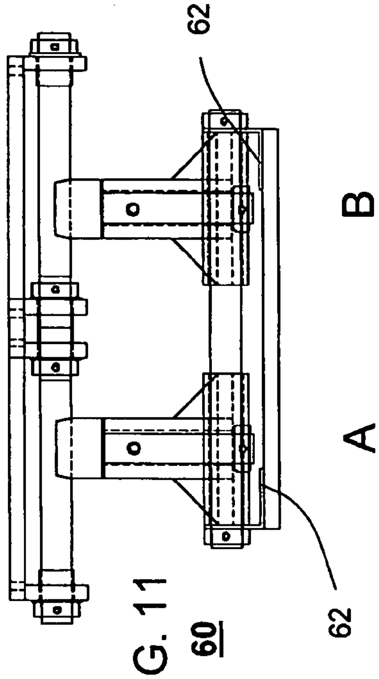
FIG. 11 is a side view of the base frame portion showing a forward and backward sliding adjustment of the base-frame portion in accordance with an embodiment of the present invention.
Figure 18:
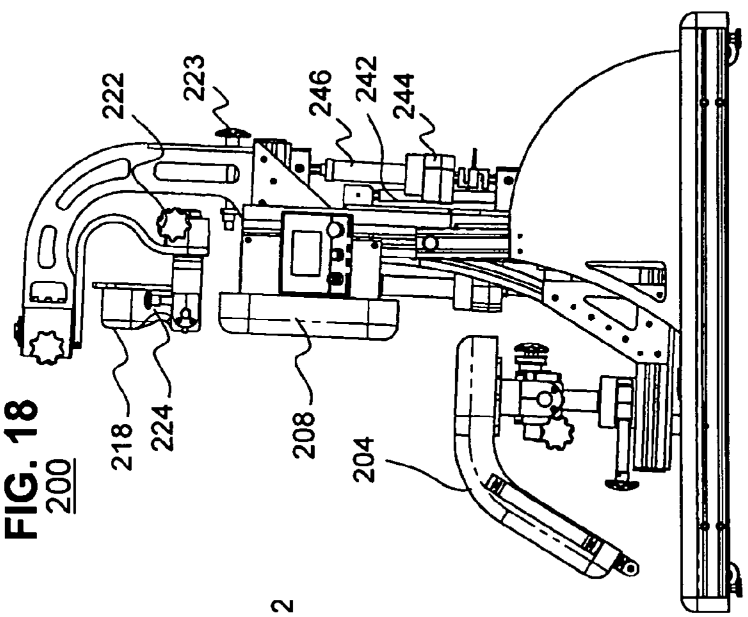
FIG. 18 is a left side view of the traction table of FIG. 13 in accordance with an embodiment of the present invention.
Figure 17:
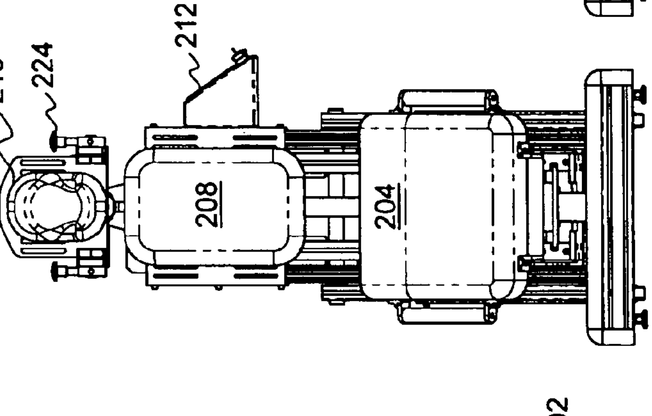
FIG. 17 is a front plan view of the traction table of FIG. 13 in accordance with an embodiment of the present invention.

Referring to FIG. 3, a front plan view of the traction table 10 is shown including the seat-bottom in a normal or un-tilted position. The seat bottom 18 is shown in a tilted position to the right from the perspective of a user in FIG. 4 using the seat bottom base plate assembly 17 which can pivot along pivot point 50. Likewise, the seat bottom can tilt along pivot point 50 to the left from the perspective of the user again using assembly 17. A more detailed view of the seat bottom base plate assembly 17 is shown in side views in FIGS. 16 and 17. Note, the assembly 17 includes a base plate 52 that pivots or tilts forwards and backwards along pivot point 50. In FIG. 18, a top view of the assembly illustrates a pivot point 54 about which the base plate 52 rotates. Lateral or forward and backward movements of the seat bottom can be achieved using an assembly 60 that includes the seat bottom base plate assembly 17 and seat bottom base guide 62 as shown in FIGS. 9-11. The assembly 17 can ride along the base guide 62 and be adjusted in place anywhere from position A to position B as shown in FIG. 11.

Figure 12:
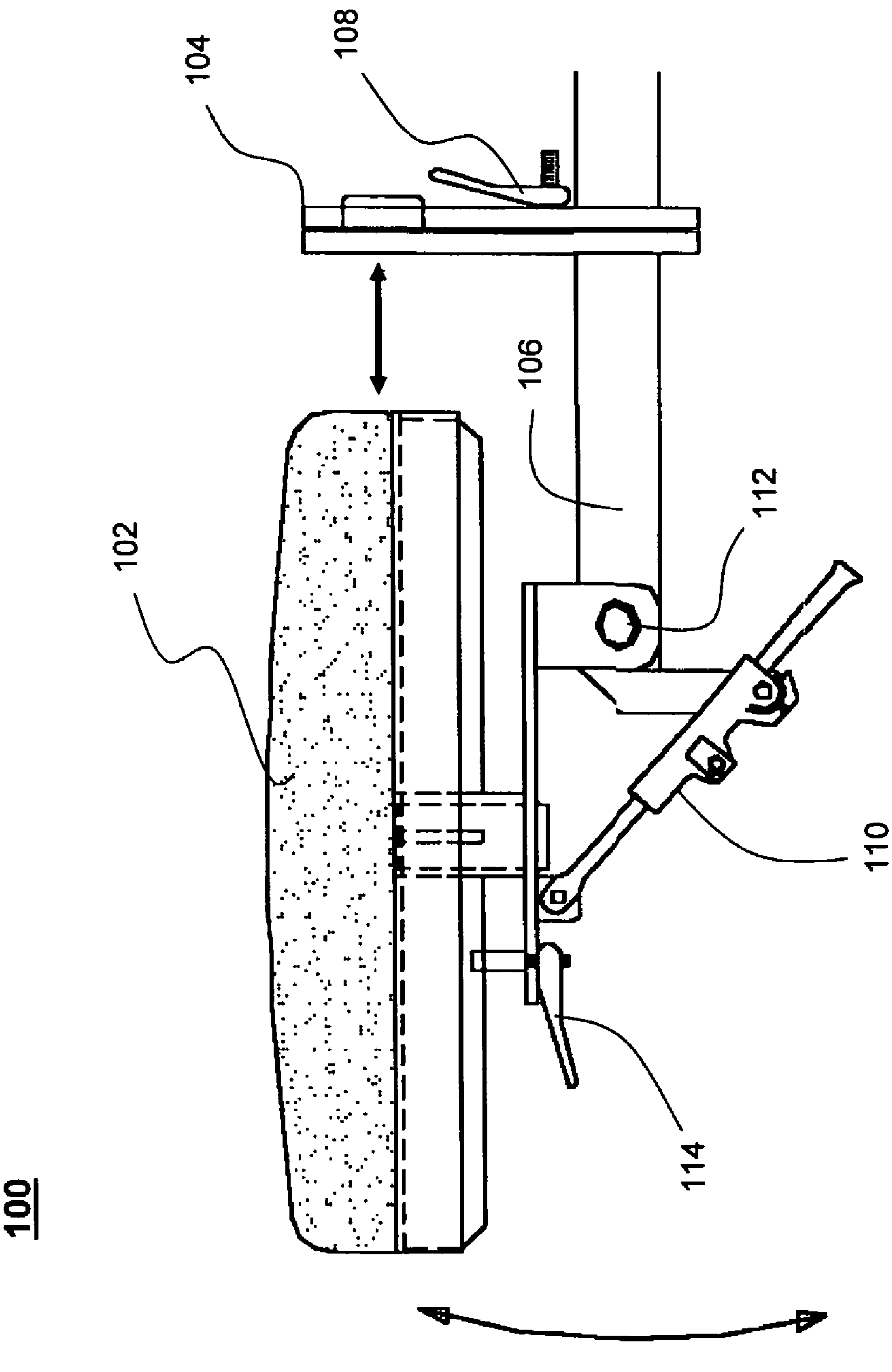
FIG. 12 is an enlarged side view of a seat-bottom that can be used with a traction table in accordance with an embodiment of the present invention.

In an alternative embodiment as shown in FIG. 12, an alternative seat bottom assembly 100 can also provide similar lateral, tilting, and rotational movements as the assembly 60 of FIGS. 9-11. The assembly 100 can include a number of locking levers such as locking lever 114 which prevents rotational movement of a seat bottom 102. A locking lever 104 on vertical member 104 can provide adjustments in a lateral or axial direction (backwards and forwards) of a tube member 106. Locking lever 104 can also enable the tilting adjustments left and right by selectively preventing the rotational movement of the tube member 106 at a desired position. Backward or forward tilting of the seat bottom 102 along a pivot point 112 can be achieved using a met lock 110. The met lock is a cable operated device that includes a release lever that can be conveniently placed remote from the axis of rotation. Note, in each instance for rotational, tilting, and lateral movements, mechanical stops can be included to limit motion to particular increments as needed.

Referring to FIGS. 13-24, another embodiment of a traction table 200 in accordance with the present invention is shown. As in the previous embodiment, the traction table 200 includes a base frame structure 202, a top frame structure 250, a seat bottom 204, and a seat back 208. The seat back 208 can be fixed to the top frame structure 250. The top frame structure 250 in this particular embodiment includes several members forming a bracketed "L" shape. The traction table 200 can further optionally include a cervical or head piece 210 having a head rest cushion 218. As can be seen in FIG. 2, the top frame structure 250 can pivot or recline at pivot point 214 relative to the base frame structure 202. In this regard, the traction table 200 can operate similar to a recliner or executive chair allowing a clothed patient to sit down into the chair. The traction table 200 can further include a plurality of actuators and locking mechanisms for customized positioning of the traction table 200 and for traction therapy as will be further discussed.

Figure 13:
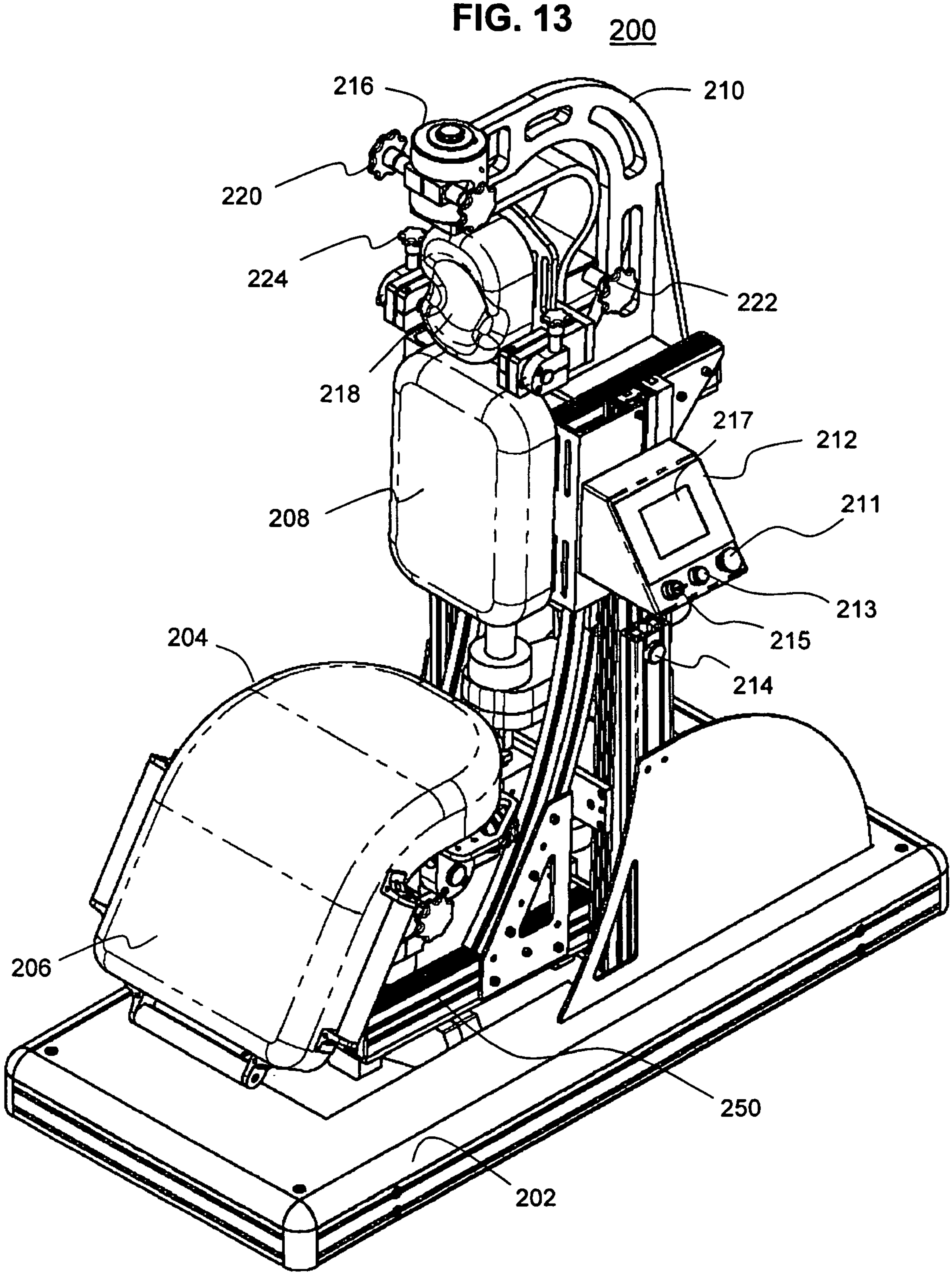
FIG. 13 is a perspective view of another embodiment of the traction table in a vertical position in accordance with an embodiment of the present invention.
Figure 14:
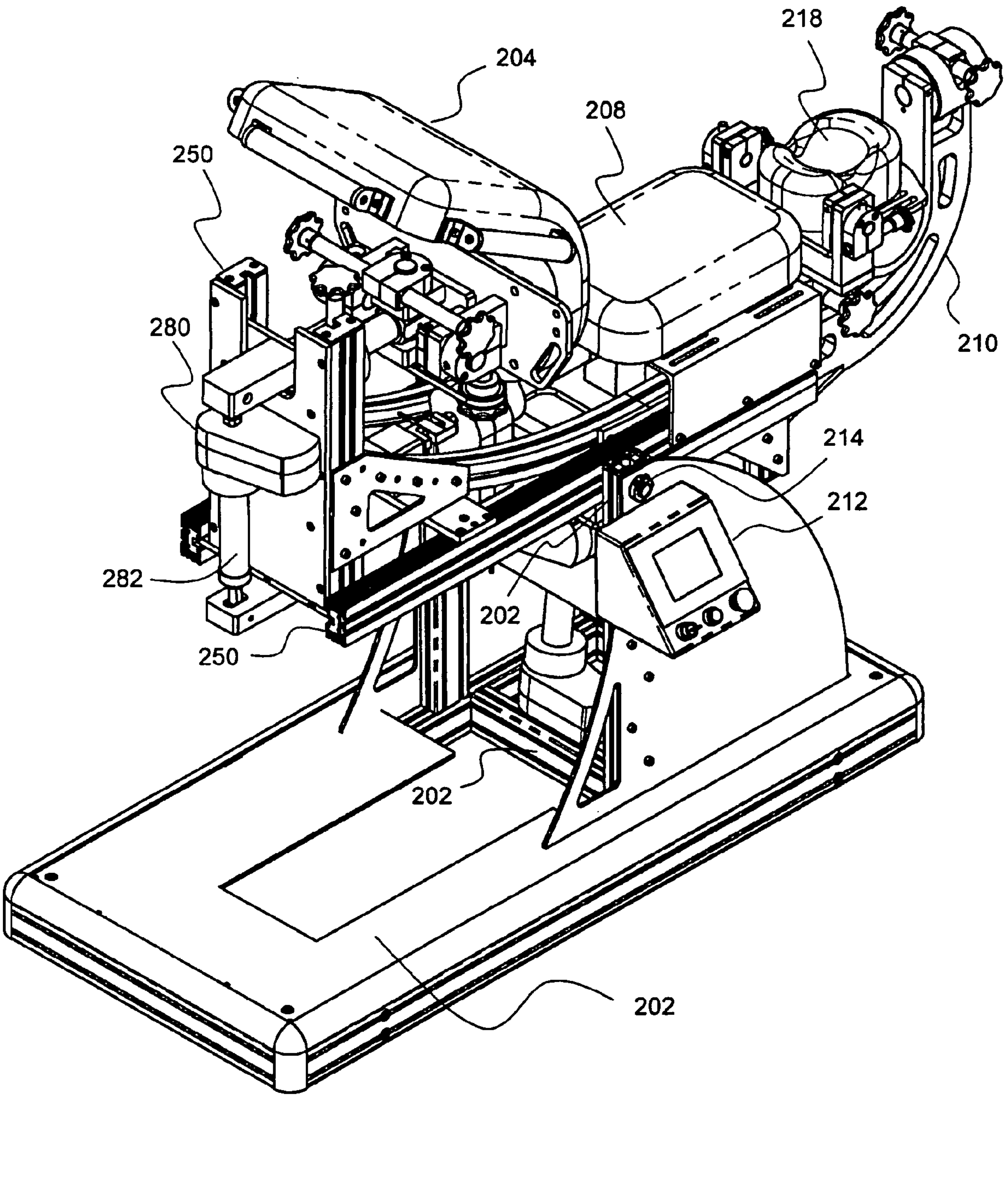
FIG. 14 is a perspective view of the traction table of FIG. 13 in a reclined position in accordance with an embodiment of the present invention.
Figure 15:
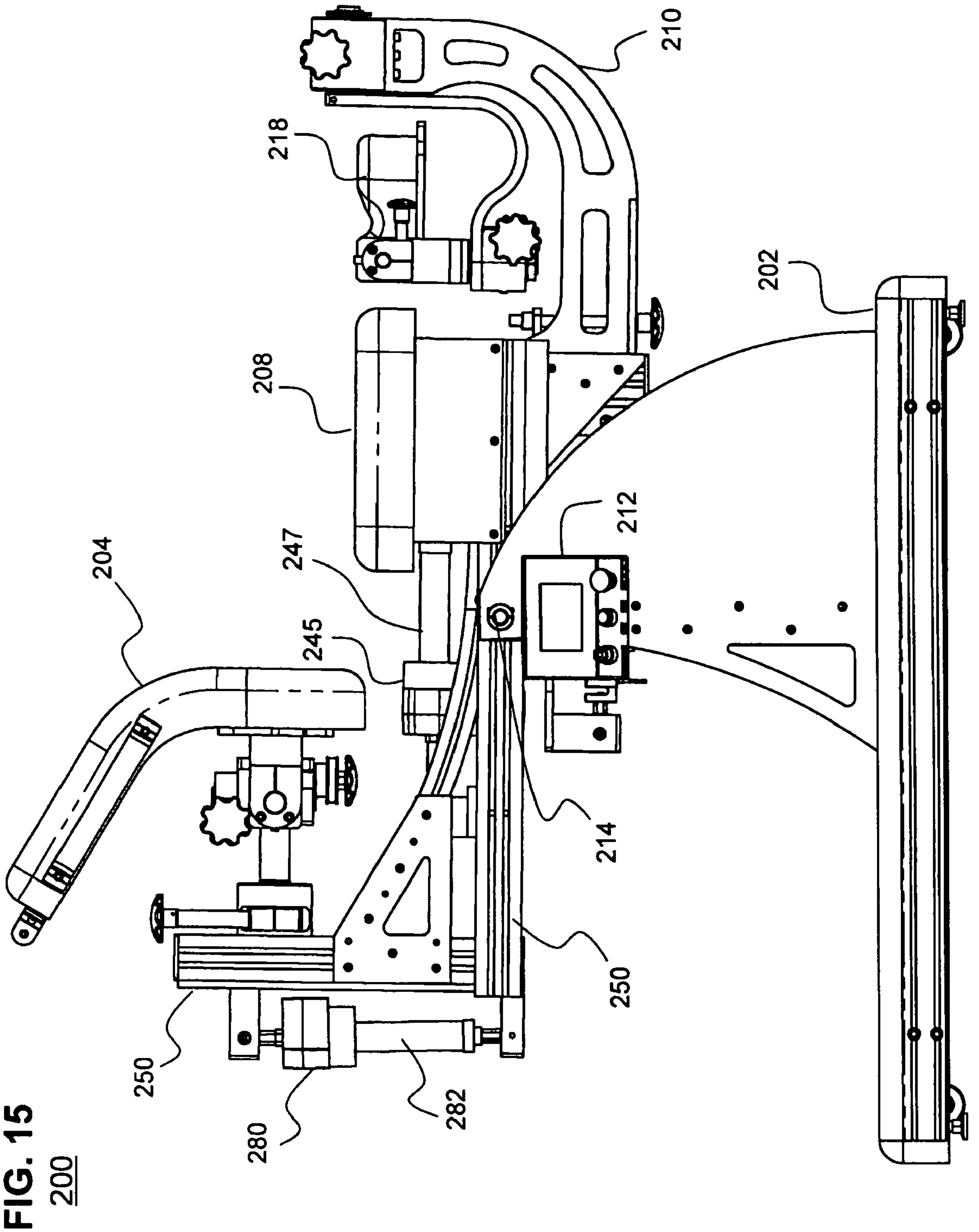
FIG. 15 is a side view of the traction table of FIG. 14 in accordance with an embodiment of the present invention.
Figure 16:
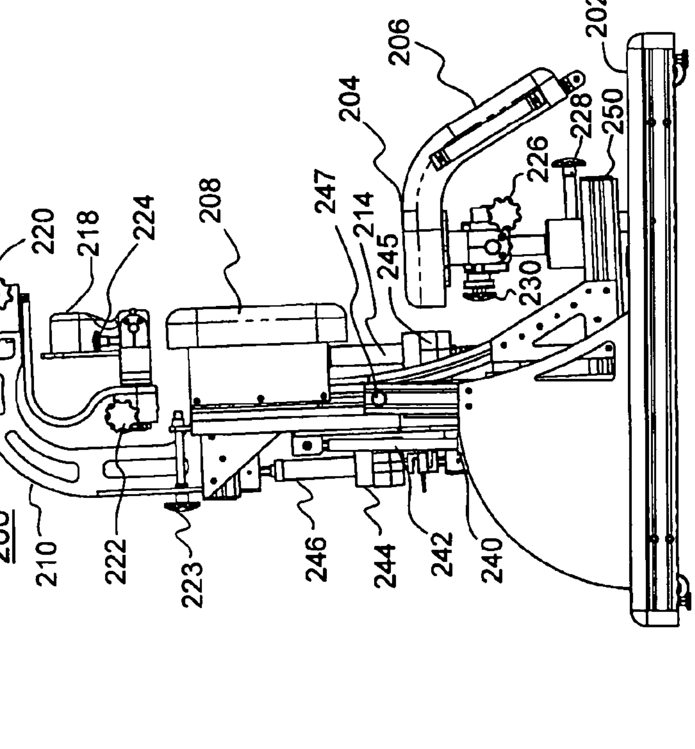
FIG. 16 is a right side view of the traction table of FIG. 13 in accordance with an embodiment of the present invention.
Figure 22:
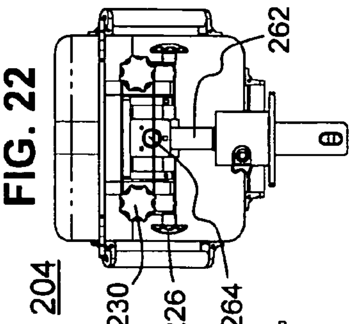
FIG. 22 is a rear plan view of the seat bottom of the traction table of FIG. 13 in accordance with an embodiment of the present invention.
Figure 21:
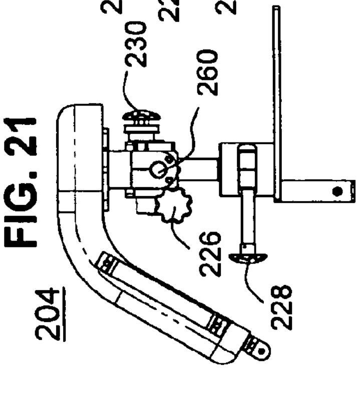
FIG. 21 is a left side view of the seat bottom of the traction table of FIG. 13 in accordance with an embodiment of the present invention.
Figure 20:
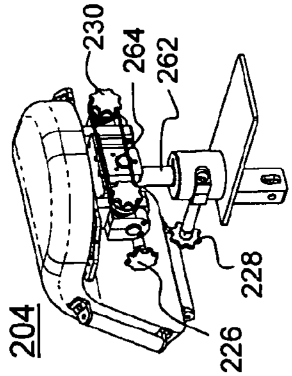
FIG. 20 is a rear perspective view of the seat bottom of the traction table of FIG. 13 in accordance with an embodiment of the present invention.
Figure 19:
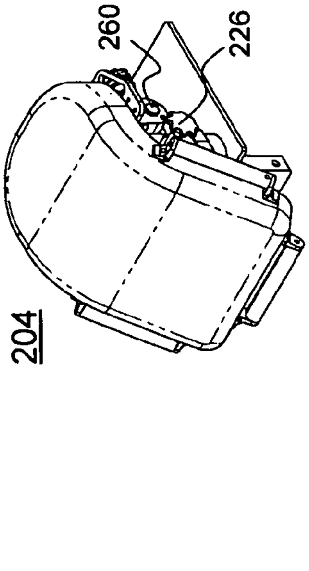
FIG. 19 is a front perspective view of a seat bottom of the traction table of FIG. 13 in accordance with an embodiment of the present invention.

The actuators can be electric driven motors or pneumatic based or any other type of actuator such as a worm gear that provides the relative controlled movement required herein. Although any number of actuators can be used, the traction table 200 illustrates up to four actuators. Referring to FIGS. 14-18 in particular, an actuator 240 and corresponding piston tube 242 enables the reclining or pivoting movement of the top frame portion or structure 250 relative to the bottom frame structure 202. An actuator 244 and corresponding piston tube 246 enables the relative parallel movement (up and down or vertical when the chair is in a vertical position) of the neck piece 210 relative to the top frame structure 250. Since the seat back 208 is fixed to the top frame structure 250 in this embodiment, an actuator 245 and corresponding piston tube 247 can enable the parallel movement between the seat bottom 204 and the seat back 208 (or top frame structure 250). Another actuator 280 and its corresponding piston tube 282 enables the relative backwards and forwards lateral movement of the seat bottom 204 relative to a vertical member of the base frame structure 250 when the traction table is in a vertical position as shown in FIGS. 13, 16, or 18. With reference to the reclined position shown in FIG. 25, the actuator 280 can also be thought of as providing parallel relative movement to another member of the base frame structure 250 since the base frame structure 250 has multiple members forming a bracketed "L" shape. As can be seen in FIG. 13, the traction table 200 further includes a controller 212 for controlling the function of the actuators. The controller 212 can include a display 217 or other form of presentation device (e.g., a speaker) and a plurality of switches and knobs 211, 213, and 215 for enabling, activating and otherwise controlling the actuators in a prescribed manner. Note, the control circuitry in one embodiment for the seat-bottom actuator motors (245 and 280), the neck piece actuator motor (244) and the chair recline actuator motor (240) can all be powered by a 110VAC input to a 24VDC output transformer.

As mentioned above, the traction table 200 includes a plurality of locking mechanisms to customize the positioning of the traction table 200. The seat bottom 204 and the neck piece 210 each have multiple degrees of freedom for custom positioning including left and right tilting, forward and backward tilting, rotation, backwards and forwards lateral movement in addition to the relative parallel movement relative to the top frame structure 250 discussed above. With particular reference to the front perspective view of FIG. 19, the rear perspective view of FIG. 20, the left side view of FIG. 21, and the rear plan view of FIG. 22, the seat bottom 204 includes a locking mechanism 226 that enables left and right tilting adjustments along a pivot point 264. Another locking mechanism 228 enables rotational adjustments of the seat bottom 204 by locking a tube 262 in place. Yet another locking mechanism 230 enables forwards and backwards tilt positioning along a pivot point 260 as particularly shown in the left side view of FIG. 21.

Figure 24:
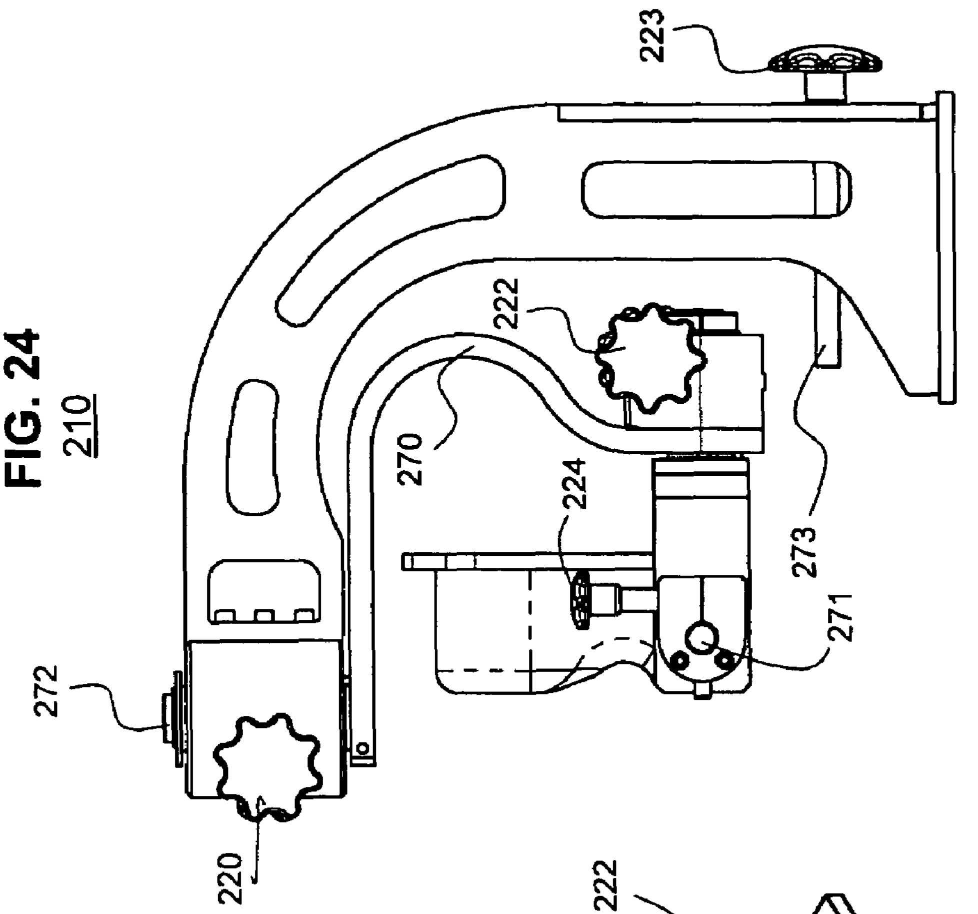
FIG. 24 is a side view of the head piece of the traction table of FIG. 13 in accordance with an embodiment of the present invention.
Figure 23:
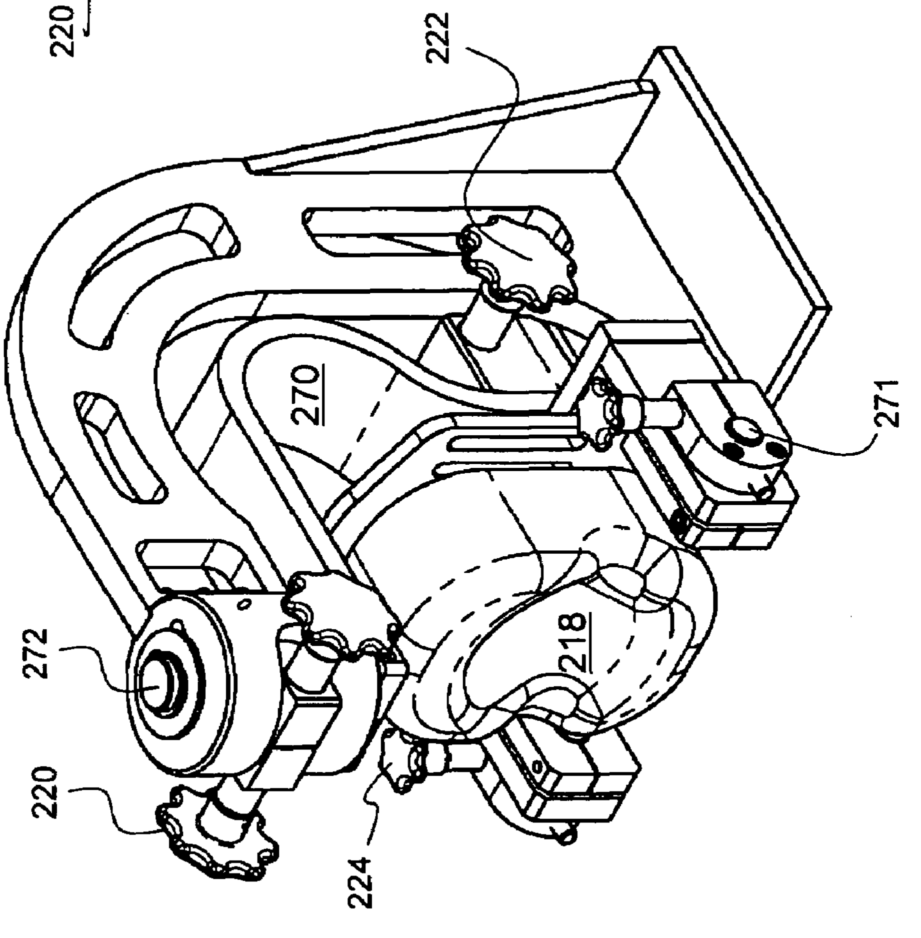
FIG. 23 is a perspective view of a head piece of the traction table of FIG. 13 in accordance with an embodiment of the present invention.

Similarly, the detailed perspective view in FIG. 23 and side view in FIG. 24 of the neck piece 210 illustrates locking mechanisms that provide custom positioning in multiple planes. A locking mechanism 220 enables rotational positioning of the head rest portion 218 and corresponding head rest frame member 270 along a pivot point 272. A locking mechanism 224 enables the forward and backward tilt positioning of the head rest portion 218 along a pivot point 271. Another locking mechanism 222 enables the left and right tilt positioning and the forward and backward lateral movement of the head rest portion 218. Yet another locking mechanism 223 enables the left and right tilt positioning of the entire neck piece 210.

Operationally, for low back traction once a patient is sitting in the traction chair 200, the seat bottom 204 can be mechanically raised to its highest level by an actuator motor. This raises the patient up. Then a strap (not shown in this embodiment) such as a 3" wide Velcro vinyl strap can secure the lower rib cage/thorax onto the seat-back 208. Next a second strap (such as a 3" Velcro vinyl strap) can secure the pelvic iliac crest of the patient onto the adjustable seat-bottom 204 and yet another strap (such as a 3rd Velcro vinyl strap) can secure the distal thigh just above the knee to the adjustable seat-bottom 204. For increased patient comfort, the traction table 200 can be reclined from its fully upright posture to a full recline position with the seat back 208 parallel to the floor or the traction table 200 can be stopped at any point within its recline arc. As mentioned above, reclining can be achieved manually or by use of the actuator motor 240 controlled by a key pad button (211, 213, and/or 215) on the controller 212. Further note, that during low back traction, the cervical traction unit or neck piece 210 can be removed and exchanged with a flat padded headpiece to improve patient comfort. The forehead is not necessarily secured to the headpiece during low back traction and in most, if not all instances, should not be secured. The forehead is primarily secured during cervical-neck traction.

To begin a low back distraction force, the adjustable seat-bottom 204 can be lowered by an actuator motor 245 as shown in FIG. 16 that draws the seat-bottom 204 downward and away from the fixed seat back 208. This movement creates the distraction force. The traction-distraction force can be set to a doctor prescribed level of distraction, or it can be set to a tolerable and comfortable level determined by patient comfort (e.g., 0 to 150 pounds). A computerized control panel or controller 212 allows the operator to set the adjustable seat-bottom actuator motor 245 into the specific traction pattern determined by the doctor or qualified therapist. The controller 212 can be set for intermittent, static or pulsed traction as desired or prescribed.

To improve the patient's comfort, the adjustable seat-bottom 204 can be rotated left or right (for example, 20 degrees), and or can tilted side-to-side (for example, 20 degrees). If the patient's thighs are particularly long, the adjustable seat-bottom 204 can also be slid forward or backwards (for example, 0 to 6 inches) to better support the back of the patient's knees. The adjustable seat-bottom allows the doctor or therapist to accommodate low back spinal distortions. The traction forces of the traction table 200 can be controlled by either a manual foot pedal (not shown) or by the controller 212 mounted on the side of the traction table 200.

Operationally, for neck traction once the patient is sitting onto the seat-bottom 204, the seat bottom can be raised until the back of the patient's head is resting comfortably on the cushioned head rest portion 218 of the neck piece 210. The head rest portion 218 can be a vinyl or leather covered foam headpiece having a molded oval shaped indented depression that the back of the head comfortably fits into. Next, the patient can be reclined to the desired reclined or horizontal posture. After the patient is reclined and the back of the head is set comfortably into the indented depression of the head rest portion 218, an "over the forehead" strap can be used to hold the head down onto and into the head rest portion 218. A cushioned forehead Velcro strap can be used to exert pressure against the forehead to keep the back of the head comfortably in the depression of the foam-cushioned head rest portion 218. This system eliminates jaw joint and TMJ problems associated with conventional head harnesses that pulls the head from the chin and the back of the head. Next, a seat-back mounted strap can secure the rib-cage/trunk onto the seat back 208 to gently hold the patient's body against the seat-back 208. This strap is to used to minimize aberrant trunk motion during cervical (neck) traction.

For neck distraction, either the foot pedal control (not shown) or the controller 212 is used to activate the actuator motor 244 that slowly moves the neck piece 210 away from the seat back 208. This movement of the neck piece 210 away from the seat-back 208 creates the distraction force that elongates the neck. The elongation of the neck along its natural vertical axis creates the traction/distraction force. To improve the patient's comfort during the cervical (neck) traction, the neck piece 210 can be modified and repositioned in multiple planes as discussed above. For example, the head rest portion 218 of the neck piece 210 can be rotated left or right (for example, 20 degrees) and can also be tilted sideways-laterally left or right (for example, 20 degrees). The head rest portion 218 can also be tilted forward or backward (for example, 20 degrees). The adjustable neck piece 210 can be locked into any of these slight repositioned postures to improve patient comfort. Modified headpiece postures allow the doctor or therapist to accommodate patient posture distortions and or improve overall patient positional comfort levels. Spinal distortions can be accommodated using the adjustable headpiece posture mechanism. Note, the 20 degree limitations are just merely examples, and any particular embodiment herein can have a greater or less range of motion within contemplation of the scope of the claims.

With either low back traction or neck traction, several safety precautions can be built into the functionality of the traction table 200 and particularly into the controller 212. For safety purposes, no traction movements can begin until the doctor or therapist manually sets the controller 212 to either lumbar lower back traction or cervical neck traction. Treatment parameters including the strength of traction and the time can be set by the doctor or therapist and observed on the control panel display 217. The patient can end the traction session at any time by pressing a hand-held safety switch "stop" button (not shown). Once the patient presses the button, all traction forces are returned to zero. To reactivate any "de-activated" traction resulting from pressing the safety stop button, the chair's controller 212 should be manually re-set by the doctor or therapist. Further note, the length of the seat-bottom's actuator motor shaft limits the seat-bottom's range of movement. Likewise, the length of the neck piece's actuator motor shaft also inherently limits the neck piece movement.

The traction chair 10 or 200 can be designed to relieve pressures on muscular and skeletal structures that may be causing either low back or neck pain. Each treatment session can consist of the doctor or therapist recommended treatment period on the traction chair and can be designed to provide either static, intermittent or pulsed distraction forces to the cervical (neck) or lumbar (low back) area. These distraction forces are used to treat and relieve pressures on musculoskeletal structures that may be causing low back pain or neck pain. Such distraction forces helps relieve pains associated with degenerative discs, herniated discs, protruding discs, facet syndromes, vertebral/disc nerve root pressures, fixated or locked vertebral joints, sciatica and or other vertebral related nerve root pressures. The reduction of pain can be accomplished by the decompressing pressures off the intervertebral discs and by simultaneously improving the spacing between the vertebrae and their associated structures.

The traction chair 10 or 200 herein has been designed to begin all traction protocols after the patient has been positioned and strapped onto the chair-table. As a safety precaution, the traction poundage can begin at "zero" pounds since traction only begins when the actuator begins to lower the seat-bottom away from the seat back. For lumbar traction, with the patient properly "strapped in", the doctor can activate the seat-bottom actuator motor (245) with a foot pedal. Activation engages the actuator 245 to move the seat-bottom along its axis and away from the seat-back. As the actuator motor moves along its axis, the "seat bottom" distance from the seat-back increases. The further the seat bottom moves away from the seatback, the more distraction poundage is produced. The traction pull force is therefore increased the further the seat-bottom moves away from the seat-back. Conversely, as the actuator (245) begins to reverse and move the seat-bottom toward the seat-back, the distraction forces are reduced.

Regarding the distraction poundage amount, the actuator motor 245 can be chosen or designed to be capable of pulling a predetermined maximum force such as 200 pounds. The actuator motor 245 can contain a poundage sensor that relays the amount of distraction force in pull-pounds to the controller and can further provide such relevant information on the display 217. The further the seat-bottom actuator 245 moves away from the seat-back 208, the stronger the distraction force. However, if there is no patient strapped onto the chair/table, when the seat bottom moves away from the seat-back, the controller 212 will likely register zero as there is no distraction force on the sensor. The seat bottom actuator 245 will likely require a resistance on itself in order for the sensor to register poundage.

As another safety precaution, the maximum amount of actuator stroke distance can also be predetermined, for example, 6 inches. If a 200 pound distraction force is desired, it may not be attainable due to a patient's shape and size as well as to how the patient's. "holding straps" are secured. Obese patients are more difficult to "tightly" secure and strap onto the unit. If a patient is semi-loosely strapped in, or there is slack in the strapping, the result is less poundage distraction force. This is due to the increased level of "tissue movement" resulting in a level of "play" in the strapping. As a result, the maximum pulling/traction capabilities of the actuator might not be achieved. But this is not essential and serves to safeguard the patient against the possibility of too much distraction.

In practice, forces of traction can be set within a patient's tolerance and comfort level as a general recommendation. The patient's actual tolerance can be a guiding factor. What this means is the patient may tolerate 50 pounds of distraction during their first session and because they may be sore from their first session, they may only be able to tolerate 40 pounds at their second session. It is for this reason that the doctor or therapist should not necessarily pre-set any traction forces or stroke distances. Each session can begin at begin at a recommended zero pounds distraction force and the doctor or therapist can determine the distraction force subjectively and objectively for each session. Thus, in one embodiment, the traction chair 10 or 200 can require the doctor and/or qualified therapist to set and administer the initiating distraction force at the onset of each and every session. The doctor and the patient, together, determine the appropriate comfortable and tolerable level of distraction for each session. Over time, the patient's tolerances are expected to increase. This indicates a level of improved tissue elasticity, flexibility and reduced surrounding spasms. For the acute patient and the "first time" patient, distractive forces can also be set at a "less than tolerance" level and the time cycle can be set to a short period such as 15 minutes or less. Thus, regarding a quantified amount of traction distraction force in any instance, it is subjectively and objectively determined by doctor. The doctor will first objectively determine and assess and diagnose the patients' condition using whichever method he or she determines as the doctor. Based on the final diagnosis, the doctor will manually activate the traction forces and determine the appropriate therapy treatment level distraction force and time for the patient.

The initial traction force can be created when the doctor depresses a foot pedal initiating the seat-bottom actuator motor 245 to move along its axis away from the seat-back 208. This action moves the seat-bottom 204 further away from the seat-back 208. The seat-bottom to seat-back angle can remain constant throughout the distraction cycle. As the doctor applies pressure on and off the foot pedal, the actuator motor will start, stop or reverse. The foot pedal can have a 3-position toggle that activates the actuator motor to move forward or reverse. The center toggle position is the off or stop position. Once pressure comes off the foot pedal it automatically and always seeks its center "off" position. As the pedal is depressed to activate the actuator for the "away" motion of the seat-bottom, distraction begins to be felt by the patient the further the seat-bottom moves away from the seat-back. Once tolerance is reached, the foot pedal is released. The foot pedal can be intermittently depressed and released to achieve a start and stop action to the actuator. Once the desired distraction force is achieved, the doctor may then set the controller 212 to begin intermittent cycling of the actuator motor 245 and repeat the actuator's movement back and forth. The set actuator stroke motion would be maintained. The doctor can also set the controller's "session treatment time". The chair/table can have a maximum time limit run (such as 60 minutes) whether the timer is set or not. If the doctor sets the time for 12 minutes, the actuator will cycle for 12 minutes. After the 12 minutes are timed out, the seat-bottom actuator motor 245 returns to its pre-distraction neutral position and can shut itself off. The patient straps would be manually disengaged by the doctor or therapist and the chair table is raised from its reclined position to its upright "start" position. The patient can then stand up off the unit the same way one stands up from a chair.

If the doctor wanted to continue the distraction session, the actuator can be re-set using the foot pedal and the timer can be re-set using the controller 212. It is up to the doctor or therapist to determine if the distraction force should be increased or decreased during the session. The doctor or therapist can do either using the foot pedal or the controller 212. If the doctor decided to increase the distraction force, this would be done by increasing the actuator stroke distance using the foot pedal or alternatively the controller 212. Note, once the foot pedal is depressed or the controller is adjusted either forward or reverse, the controller can be programmed to interrupt the automatic actuator cycling. The doctor would need to re-set the actuator to begin cycling using the controller 212. The adjusted actuator stroke distance would automatically be remembered by the controller 212. The cycle is finished after the controller timer counts down. The doctor can increase or decrease the time during the session using the controller 212. The actuator distance adjustment "reset" feature is designed to work in either an increase mode or decrease mode. The increased stroke distance has the effect of increasing the distractive force or distraction poundage. Once the new increased tolerance was set by the doctor, the doctor could then re-engage the automatic cycling using the controller 212 and the controller 212 will remember the newly adjusted stroke distance and time. If the time was not re-set after the stroke distance was re-set, the timer would continue to count down from where it left off prior to the newly adjusted actuator stroke distance.

During a distraction session, anytime the doctor or therapist depresses the foot pedal, the automatic active cycling of the seat-bottom actuator 245 can be programmed to disengage. In this instance, the seat-bottom 204 will no longer automatically cycle the newly adjusted distraction force. The automatic distraction cycle would be reset by the doctor. The foot pedal disengagement of the traction cycle protects the patient from distraction forces beyond their tolerance.

In light of the foregoing description, it should be recognized that embodiments in accordance with the present invention can be realized in hardware, software, or a combination of hardware and software. A network or system according to the present invention can be realized in a centralized fashion in one computer system or processor, or in a distributed fashion where different elements are spread across several interconnected computer systems or processors (such as a microprocessor and a DSP). Any kind of computer system, or other apparatus adapted for carrying out the functions described herein, is suited. A typical combination of hardware and software could be a general purpose computer system with a computer program that, when being loaded and executed, controls the computer system such that it carries out the functions described herein.

In light of the foregoing description, it should also be recognized that embodiments in accordance with the present invention can be realized in numerous configurations contemplated to be within the scope and spirit of the claims. Additionally, the description above is intended by way of example only and is not intended to limit the present invention in any way, except as set forth in the following claims.

What is claimed is:

1. A traction table, comprising:

a frame having a base-frame portion rotatably coupled to a top-frame portion;

a seat back portion coupled to the top frame portion, wherein the seat back portion reclines where it pivots with the base-frame portion of the frame; and a seat-bottom slidably coupled to the frame top portion, wherein the seat-bottom at least moves parallel relative to the top-frame portion;

a head piece coupled to the tor frame portion that moves vertically relative to the seat back portion and selectively provides intermittent or pulsed traction to the neck via an actuator; and wherein the head piece is further constructed to rotate, tilt side to side, tilt forward and backward, and move perpendicularly forward and backwards relative to the seat back portion.

2. The traction table of claim 1, wherein the seat-bottom further rotates about a pivot point and tilts about at least one axis.

3. The traction table of claim 1, wherein the traction table further comprises at least one actuator motor for raising or lowering the seat-bottom relative to the top-frame portion.

4. The traction table of claim 1, wherein the seat-bottom further slides forwards or backwards relative to the top-frame portion.

5. The traction table of claim 1, wherein the traction table further comprises at least one among a strap for securing a portion of a torso to the seat back portion, a strap for securing a pelvic area to the seat-bottom, a strap for securing a thigh to the seat-bottom and a strap for securing a shin to a lower leg portion of the seat-bottom.

6. The traction table of claim 1, wherein the traction table further comprises a controller for adjusting an actuator motor for at least one among a position of the seat-bottom and a traction pattern using the seat-bottom.

7. The traction table of claim 3, wherein the traction table further comprises sensors used for automatically shunting the at least one actuator motor.

8. The traction table of claim 1, wherein the traction table further comprises at least one strap for securing a portion of a head to the head piece.

9. The traction table of claim 1, wherein the traction table further comprises at least one actuator motor for moving the head piece relative to the top-frame portion in parallel fashion.

10. The table of claim 9, wherein the traction table further comprises sensors used for automatically shunting the least one actuator motor for raising or lower the head piece.

11. A traction table, comprising:

a frame having a frame base portion rotatably coupled to a top-frame portion;

a seat back portion coupled to the top-frame portion, wherein the seat back portion reclines where it pivots with the frame base portion;

a seat-bottom slidably coupled to the top-frame portion, wherein the seat-bottom tilts side to side, rotates, slides forwards or backwards relative to the top-frame portion and moves vertically relative to the top-frame portion;

a head piece coupled to the tor frame portion that moves vertically relative to the seat back portion and selectively provides intermittent or pulsed traction to the neck via an actuator;

wherein the head piece is further constructed to adjust in among one or more planes by rotating, tilting side to side, tilting forward and backward, and laterally moving forward and backwards; and wherein the seat back portion and the seat-bottom form a seated recliner enabling tractions and distractions in a seated recliner posture.

12. The traction table of claim 11, wherein the traction table further comprises at least one among a strap for securing a portion of a torso to the seat back portion, a strap for securing a pelvic area to the seat-bottom, a strap for securing a thigh to the seat-bottom, a strap for securing a shin to a leg section of the seat-bottom, and a strap for securing a portion of a head to the head piece.

13. The traction table of claim 11, wherein the traction table further comprises at least one among an actuator motor for moving the seat-bottom relative to the top-frame portion in a parallel fashion along a “Z” axis, an actuator motor for moving the head piece relative to the top-frame portion in parallel fashion along a “Z” axis, an actuator motor for reclining the seat-back portion about an “X” axis, and an actuator motor for moving the seat-bottom relative to the top-frame portion in a perpendicular fashion along a “Y” axis.

14. The traction table of claim 13, wherein the traction table further comprises sensors used for automatically shunting at least one among the actuator motors.

15. The traction table of claim 13, wherein the traction table further comprises a controller programmed to perform at least one among adjusting of the at least one actuator motor for positioning the seat-bottom, for positioning of the head piece, for altering a traction pattern using the seat-bottom, and for altering a traction pattern using the head piece.

16. A traction table, comprising:

a seat back portion coupled to a frame;

a seat-bottom portion slidably coupled to the frame, wherein the seat-bottom portion at least moves parallel relative to the frame;

a biasing mechanism coupled to the seat-bottom portion for biasing the seat-bottom portion along a parallel plane relative to the frame;

a controller coupled to the biasing mechanism for selectively controlling the motorized mechanism;

wherein the seat back portion and the seat-bottom portion form a seated recliner enabling tractions and distractions in a seated recliner posture and wherein the seat-bottom portion and the seat back maintain a perpendicular angular relationship as the seated recliner is reclined;

a head piece coupled to the frame that moves vertically relative to the seat back portion and selectively provides intermittent or pulsed traction to the neck via the motorized mechanism; and wherein the head piece is further constructed to adjust in among one or more planes by rotating, tilting side to side, tilting forward and backward, and laterally moving forward and backwards.

* * * * *